United States Patent [19]

Luthra et al.

[11] Patent Number: 5,652,196
[45] Date of Patent: Jul. 29, 1997

[54] TIMED RELEASE OF WATER-SOLUBLE PLANT NUTRIENTS

[75] Inventors: Narender Pal Luthra, Columbia; Darwin Scott Bull, Baltimore, both of Md.; Garrard Lee Hargrove, Vacaville, Calif.

[73] Assignee: OMS Investments, Inc., Wilmington, Del.

[21] Appl. No.: 410,568

[22] Filed: Mar. 24, 1995

Related U.S. Application Data

[63] Continuation of Ser. No. 150,574, Nov. 10, 1993, abandoned, which is a continuation of Ser. No. 881,952, May 12, 1992, abandoned, which is a continuation-in-part of Ser. No. 733,891, Jul. 22, 1991, abandoned.

[51] Int. Cl.$^6$ .................... A01N 25/08; A01N 25/10; C05C 9/00
[52] U.S. Cl. .................... 504/116; 71/28; 71/64.06; 71/64.07; 71/64.11
[58] Field of Search .................... 71/64.06, 64.07, 71/64.11, 64.12, 28–30; 504/116

[56] References Cited

U.S. PATENT DOCUMENTS

| | | | |
|---|---|---|---|
| 3,223,518 | 12/1965 | Hansen | 71/64.07 |
| 3,400,011 | 9/1968 | Fox | 71/64.11 X |
| 4,015,970 | 4/1977 | Hennart | 71/11 |
| 4,019,890 | 4/1977 | Fujita et al. | 71/64.11 |
| 4,369,055 | 1/1983 | Fujita et al. | 71/64.11 |
| 4,657,576 | 4/1987 | Lambie | 71/64.07 |
| 4,670,250 | 6/1987 | Baker | 424/419 |
| 4,678,710 | 7/1987 | Sakimoto et al. | 428/407 |
| 4,851,027 | 7/1989 | Murayama et al. | 71/64.07 |
| 5,006,147 | 4/1991 | Thaler et al. | 71/27 |
| 5,089,041 | 2/1992 | Thompson et al. | 71/64.11 |
| 5,435,821 | 7/1995 | Duvdevani et al. | 71/28 |

FOREIGN PATENT DOCUMENTS

| | | |
|---|---|---|
| 88113933 | of 1988 | European Pat. Off. . |
| 93304392 | of 1993 | European Pat. Off. . |
| 954555 | 10/1960 | United Kingdom .......... 71/64.11 |
| US92/01609 | of 1992 | WIPO . |

*Primary Examiner*—Ferris Lander
*Attorney, Agent, or Firm*—Jones, Day, Reavis & Pogue

[57] ABSTRACT

Products for the variable controlled release of water soluble agents are disclosed. The products have a core of water soluble agent and a first and second coating. The first coating has a permeability such that the agent can be released at a controlled rate, while the second coating has a relatively low water vapor transmission rate. Variation in the coating thicknesses and coating conditions result in nutrient release profiles which can be tailored to specific plant requirements. After application of the product, release of the agent is negligible, but after a predetermined time, e.g. one month or more, substantial release of the agent from the coated product begins. The product is particularly suitable for delayed, controlled release fertilizers.

24 Claims, 13 Drawing Sheets

DELAY RESULTING FROM APPLICATION OF DARAN SL-159 ONTO MODIFIED OIL-COATED UREA PRILLS (50°C)

DELAY RESULTING FROM APPLICATION OF DARAN 229 ONTO MODIFIED OIL-COATED N-P-K PRILLS (50°C)

DELAY RESULTING FROM APPLICATION OF DARAN SL-143 ONTO MODIFIED OIL-COATED N-P-K PRILLS (50°C)

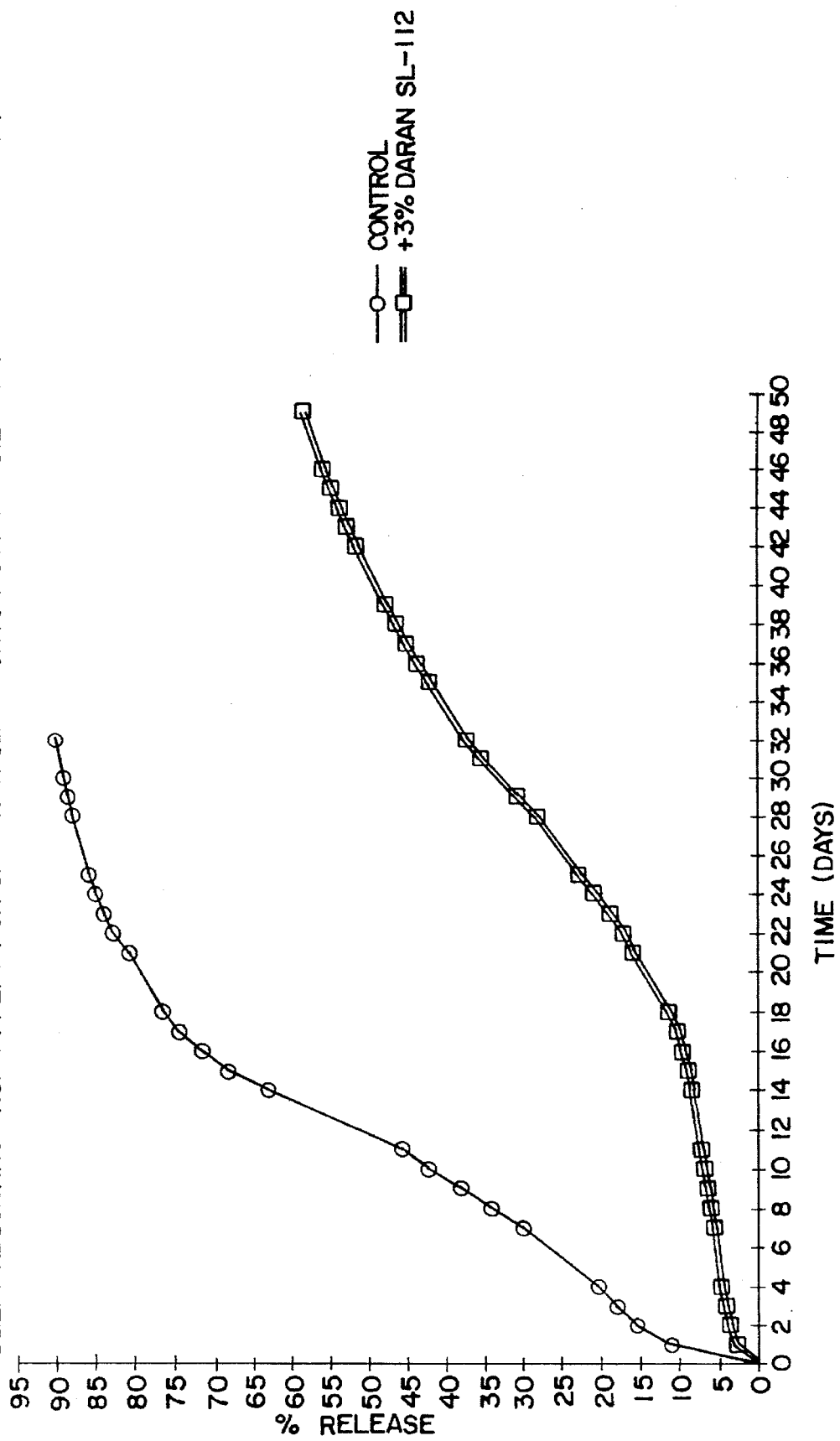

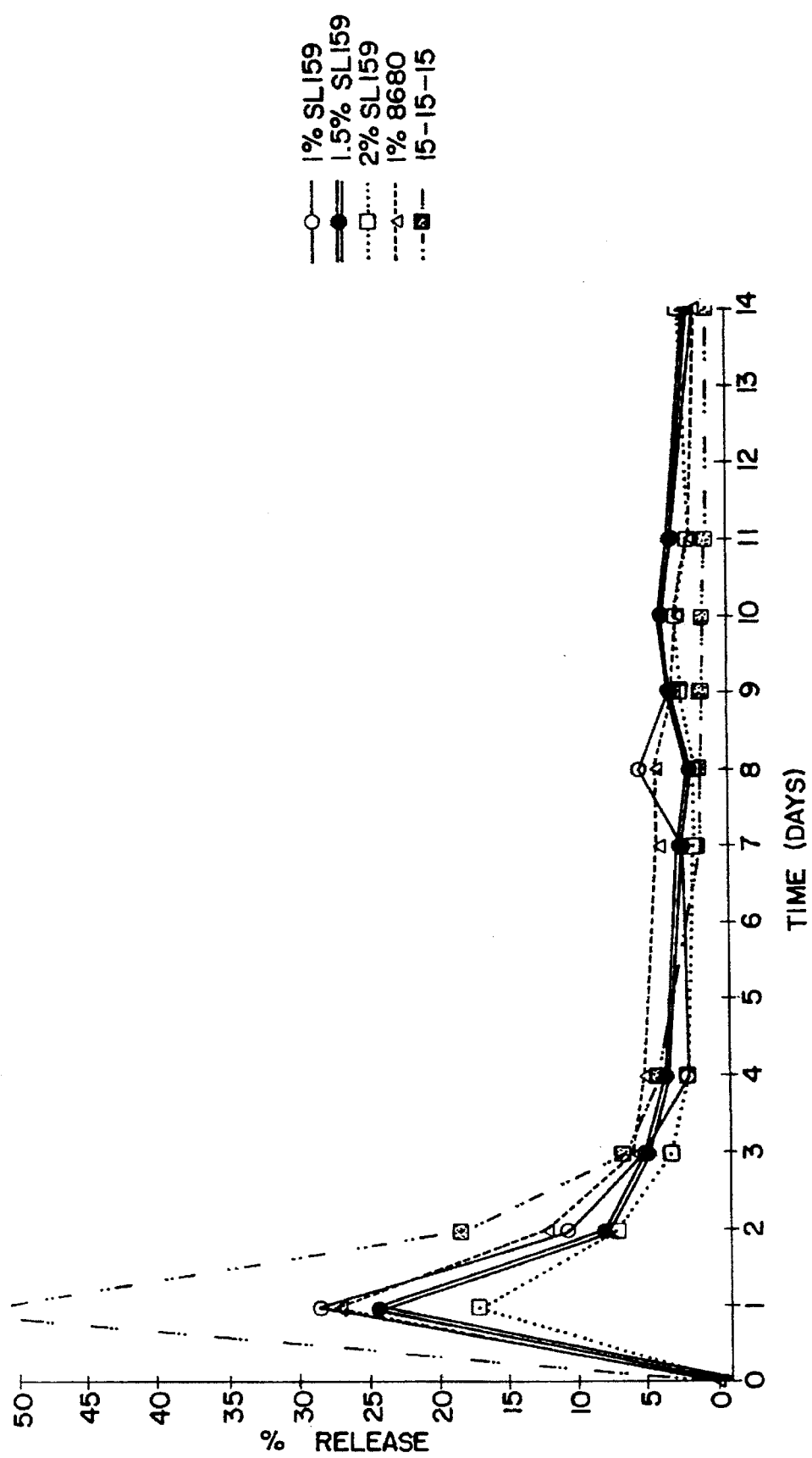

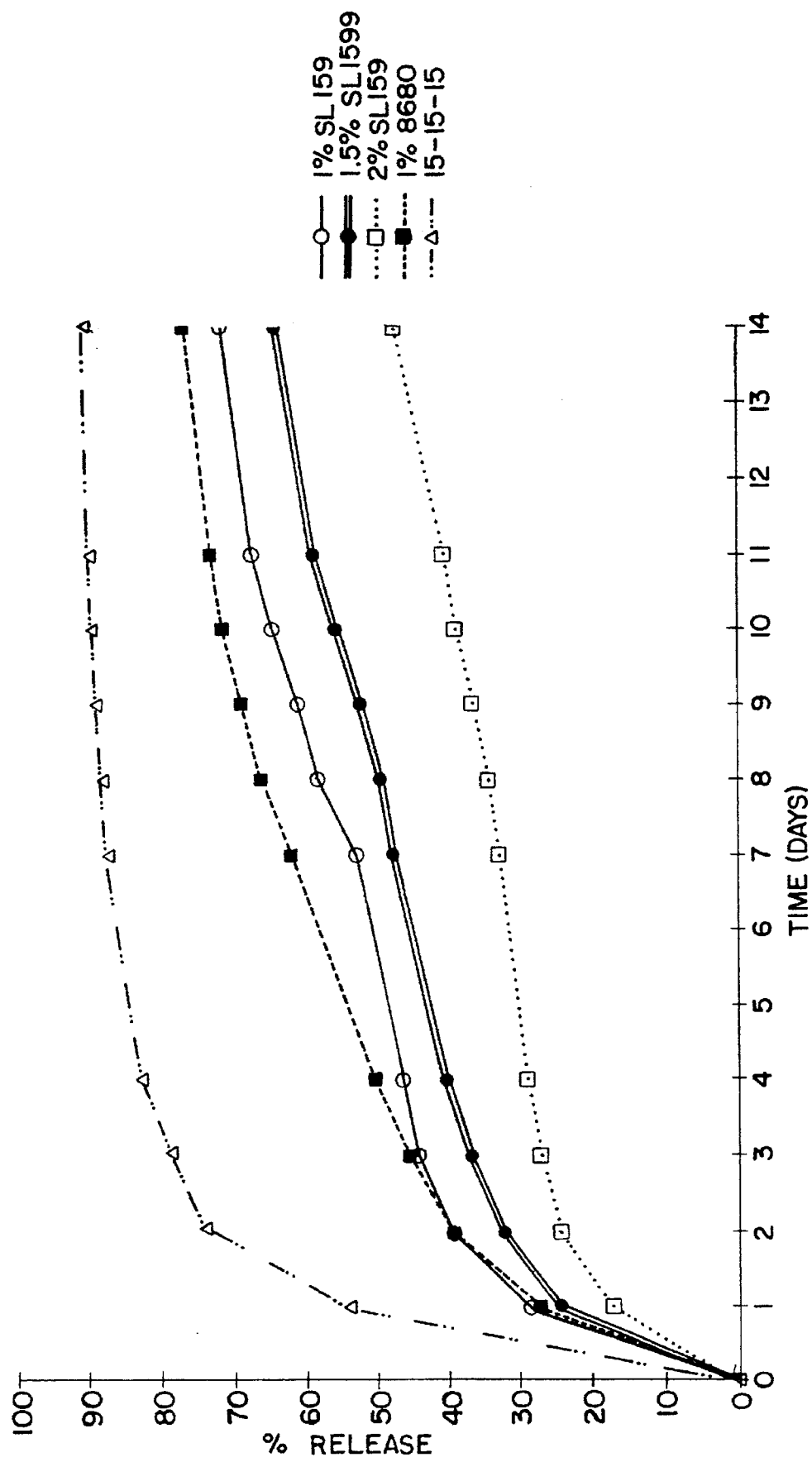

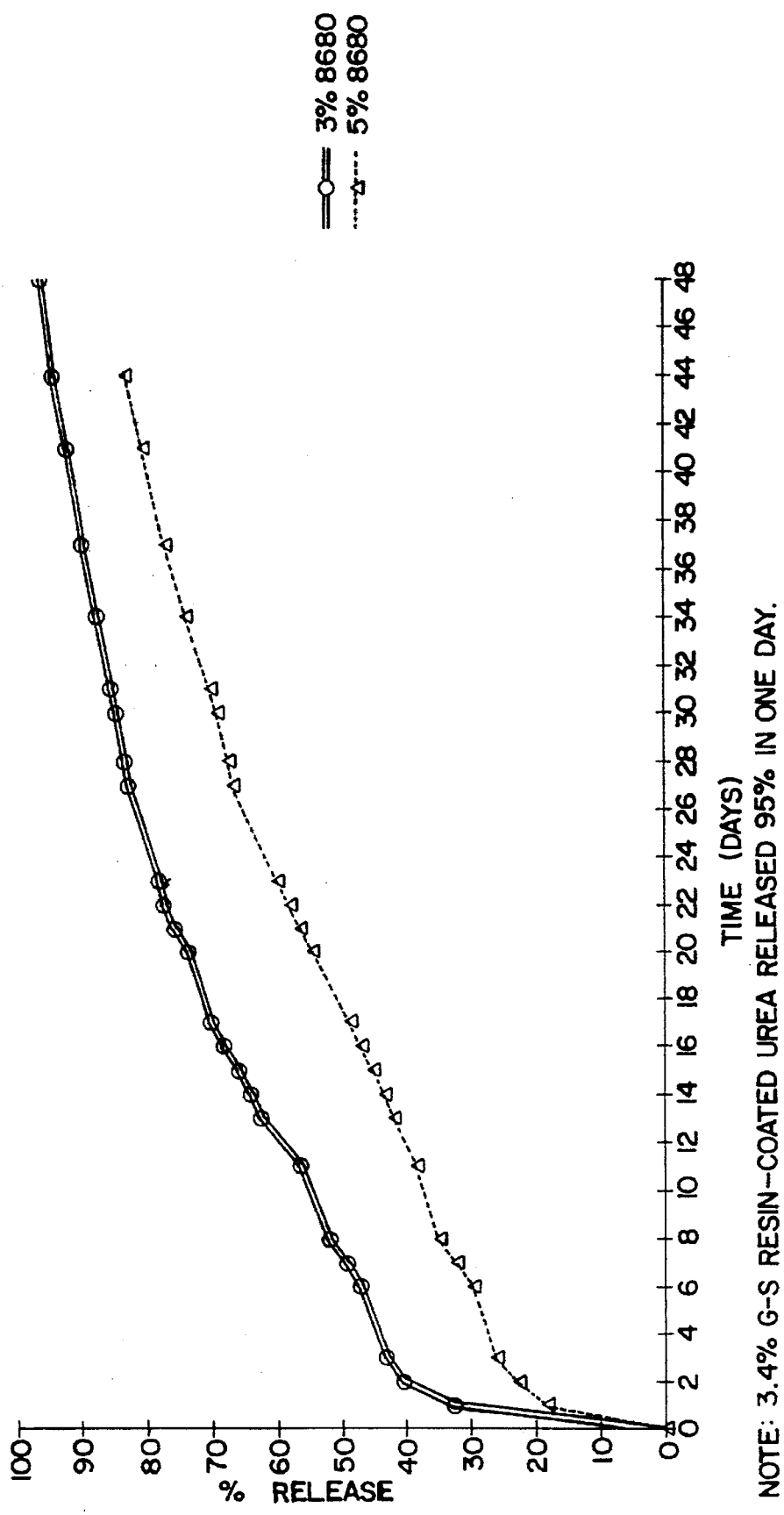

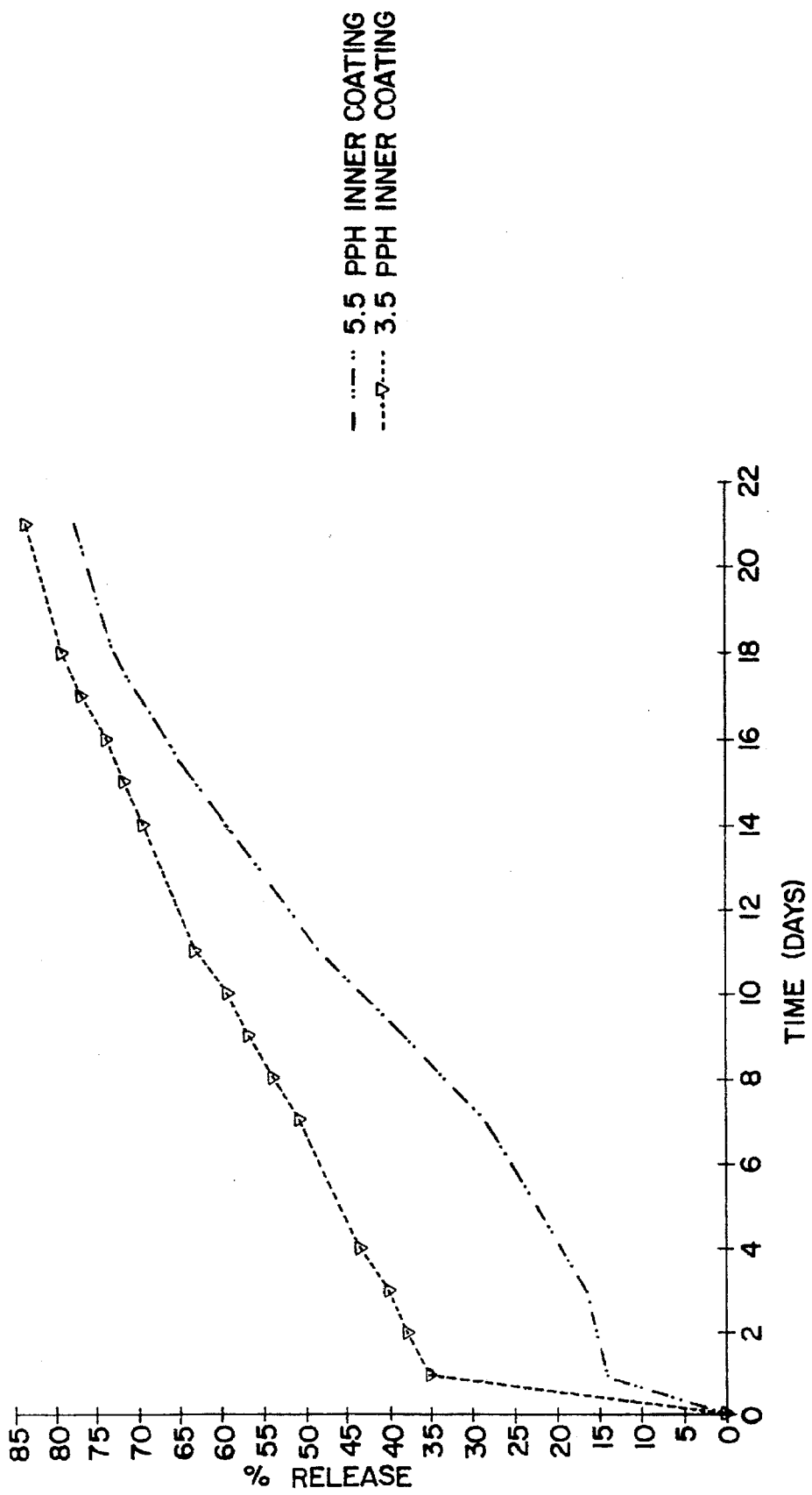

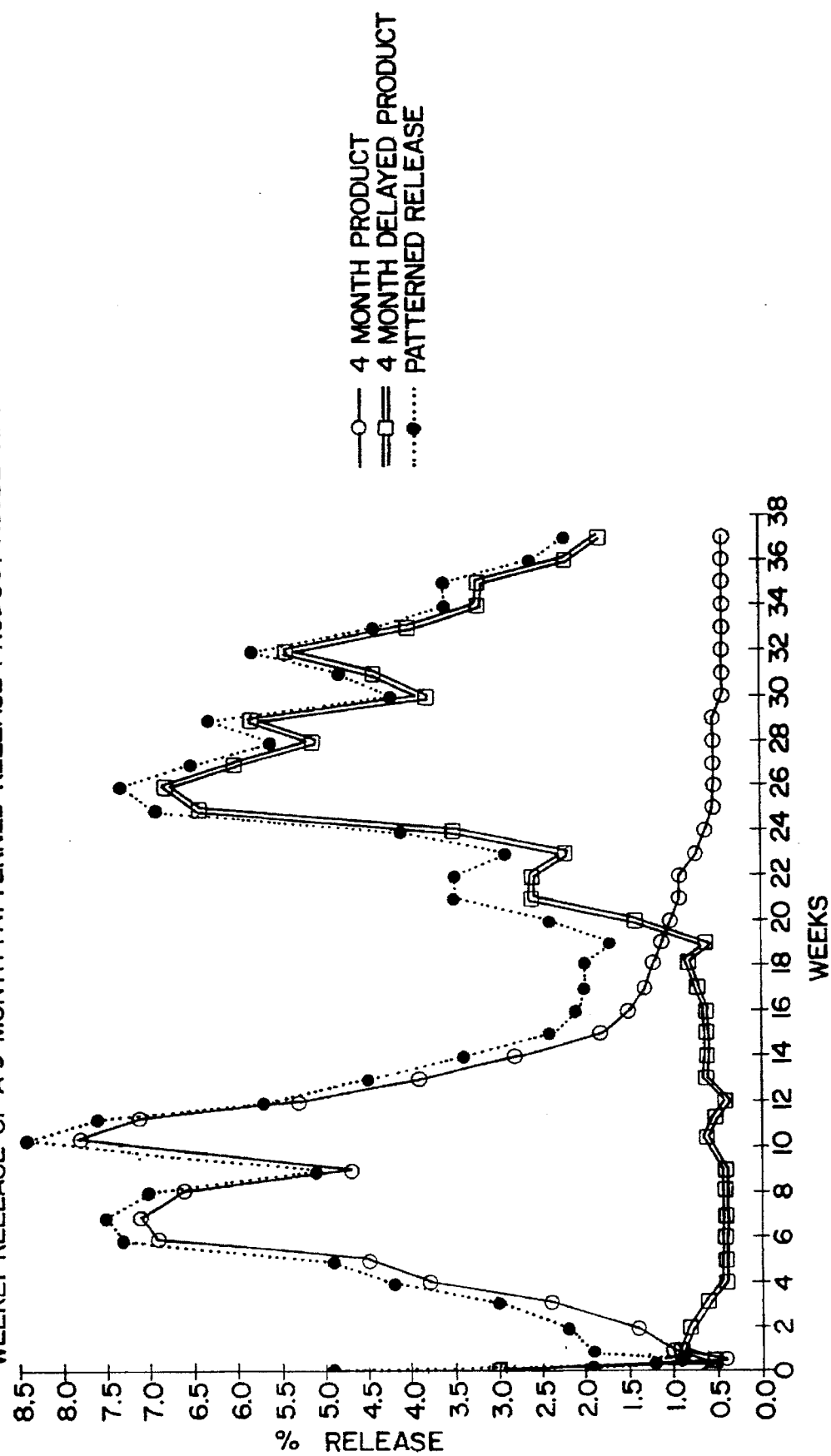

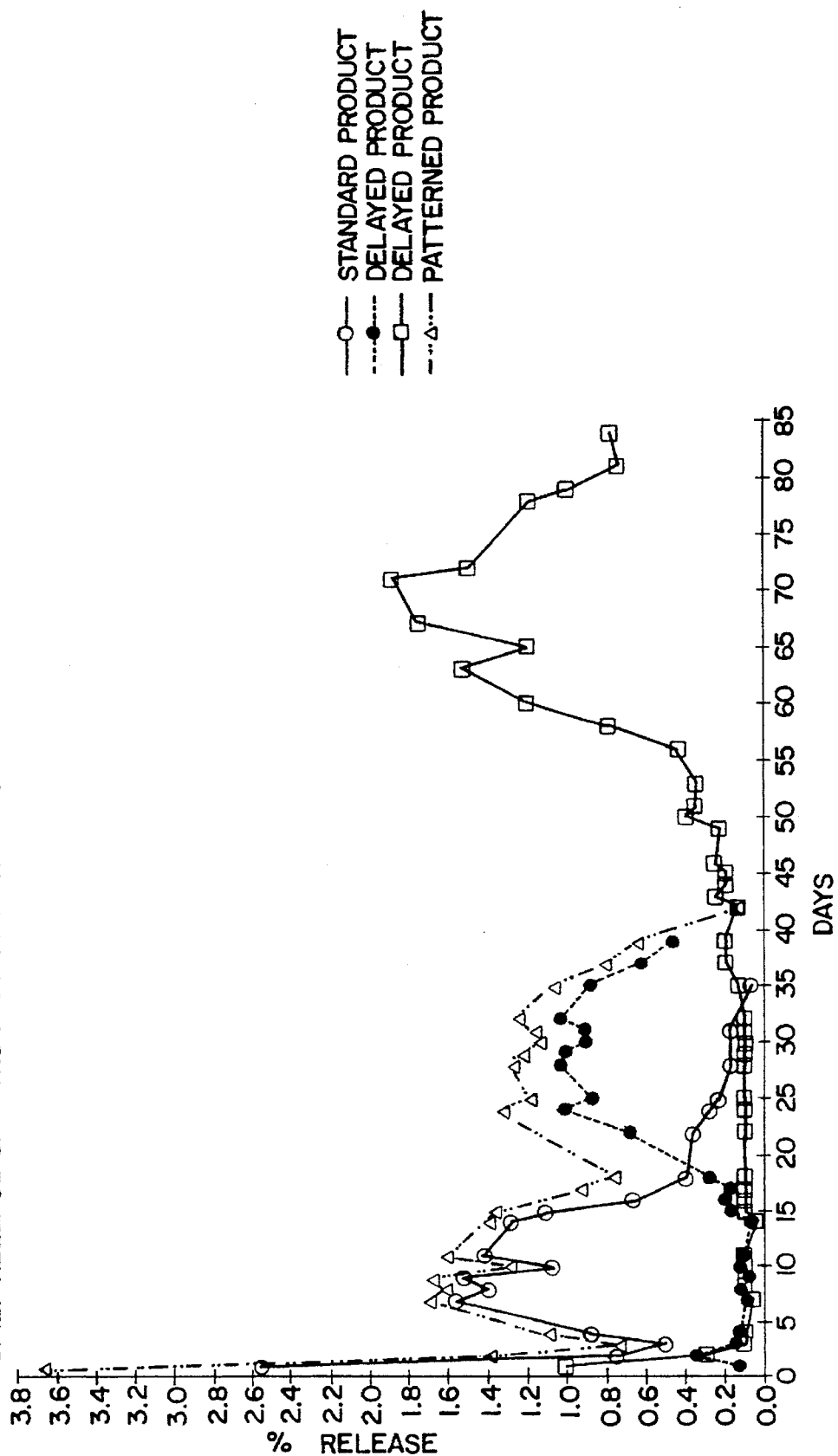

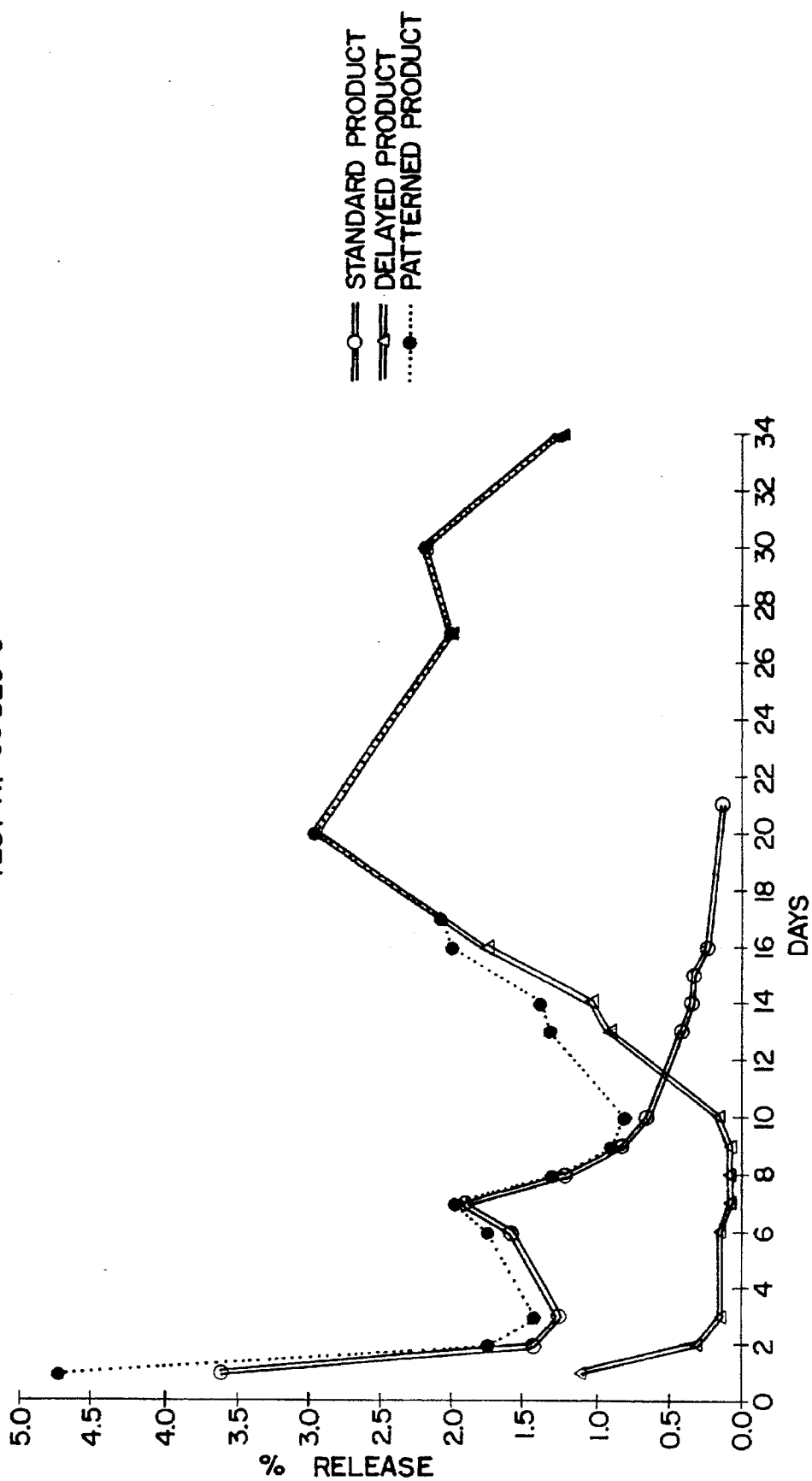

TIMED RELEASE OF WATER-SOLUBLE PLANT NUTRIENTS

This is a continuation of application Ser. No. 08/150,574, filed on Nov. 10, 1993 as a continuation of application Ser. No. 07/881,952, filed May 12, 1992, now abandoned, which was a continuation in part of application Ser. No. 07/733,891, filed Jul. 22, 1991, now abandoned.

FIELD OF THE INVENTION

This invention relates generally to products capable of releasing water soluble agents at different rates over time. Specifically, the products are fertilizers which can be packed with a seed or seedling, and release nutrients in a fashion consistent with the growing plant's needs. If necessary, the products can be made to remain dormant for a predetermined period of time before nutrient release begins.

In one embodiment, the pattern of nutrient release is such that release may be substantially delayed for a predetermined period of time followed by a period of relatively high release.

In another embodiment, a period of relatively high initial release is followed by a period of relatively low, constant release. In yet another embodiment, a period of high initial release is followed by a period of very low release and then a second period of relatively high release. Since both the relative amount and timing of nutrient release can be predetermined, it is possible to fertilize plants once per year or two without fear of damaging the plants or harming the environment.

BACKGROUND OF THE INVENTION

True control over the rate of nutrient release by fertilizers has long been known to be a desirable but elusive goal. A plant's need for nutrients changes from season to season, and species to species. As a result farmers, foresters and gardeners have generally relied on the use of repeated, timed doses of fertilizers in an effort to obtain optimal plant growth. A fertilizer product tailored to a plant's specific needs over a relatively long period of time, would eliminate the need for one or more doses.

Such products would be of great value to nurserymen and foresters, the first because current methods of fertilizing are labor intensive, and the latter because such products could greatly increase the rate of seedling survival.

The invention generally relates to products capable of releasing of water soluble agents such as those exhibiting delayed, controlled release and those having a relatively high initial release followed by a relatively low, constant release. A "delayed, controlled release" is defined as a release for which onset is substantially delayed for a predetermined period of time. Upon onset of release, the agent is released at a controlled rate.

This invention is particularly related to the timed release of agents suitable for cultivating horticultural growth, e.g. fertilizer products. By the term "horticultural", it is meant to include not only the science of growing fruits, vegetables, flowers or ornamental plants, but also to include, but not necessarily to limit to, silviculture, i.e. a branch of forestry dealing with the development and care of forests, and the science of cultivating grasses such as home lawns.

Controlled release products have become an important tool in many fields. It is well known that controlling the rate of release of an active agent from its carrier product maximizes the agent's effect on its target and minimizes potentially harmful side effects. In other words, if it is known that the target not only requires the agent's presence at the time the product is applied, but that the agent will also be required over a specific period of time after the initial application, the product can be modified so that agent is released over the period of time mandated. Products employing controlled release have been used in many fields including, but not necessarily limited to, agriculture, health care, personal care and hygiene, and pharmaceuticals.

In the agricultural field, controlled release products are used to deliver fertilizer, herbicidal and pesticidal agents to crops to maximize the agent's effect over the crop's growing season. See U.S. Pat. No. 3,223,518 issued to Hansen Dec. 14, 1965; U.S. Pat. No. 4,019,890 issued to Fujita et al. Apr. 26, 1977; U.S. Pat. No. 4,015,970 issued to Hennart Apr. 5, 1977; and U.S. Pat. No. 4,851,027 issued to Murayama et al. Jul. 25, 1989. For instance, it is well known that crops in the early stages of development are harmed by heavy doses of fertilizer. In the past, a program comprising several light applications over the growing season had been recommended to solve that problem. However, such programs can be difficult to follow because of the increased labor costs and the incidental crop damage caused by equipment moving through the field during applications which occurred late in the program. Furthermore, when water soluble fertilizers are applied to open fields, some of the fertilizer is washed into the local drainage system by rainwater runoff. This portion of the fertilizer is ineffective for its intended use and can significantly pollute nearby waterways and reservoirs.

As a result, controlled release products which delivered fertilizer at rates which attempt to approximate a program of several light applications have been developed. To a large extent, these products are made by coating fertilizer granules or prills with various materials to reduce the rate of release of the fertilizing agent.

For instance, U.S. Pat. No. 3,223,518 issued to Hansen Dec. 14, 1965 discloses coatings of polymer resins exemplified by linseed oil- or soybean oil-based resins, e.g. linseed oil-based copolymers with dicyclopentadiene. The release rates of the coated products described in the '518 patent depend on various factors, some of which include the number of coatings applied to the product, or the coating's thicknesses, and the type of polymer used in the coating. The controlled release rates obtained from those coated products range from 55% of the fertilizer being released in 24 hours down to about 0.05% in 120 hours. As the graphs which appear in the '518 patent illustrate, the release rates for these coated products can be varied and can be described as a continuous release which begins upon application of the fertilizer product. In other words, the onset of release occurs almost immediately upon application of the fertilizer product and typically within a week of being applied. A fertilizer product exemplifying this type of controlled release is available as Osmocote® fertilizer from Grace-Sierra Horticultural Products Co.

Another type of coated fertilizer product employs additives to effect controlled release. U.S. Pat. Nos. 4,019,890 and 4,369,055 issued to Fujita Apr. 26, 1977 and Jan. 18, 1983 respectively, describe polyolefin resin coatings that contain hydrophilic powder additives and surfactants which, due to their water-compatibility, create pores within the resin coatings upon contact with soil moisture. However, due to the water-insolubility of the coating resin, e.g. thermoplastics such as polyethylene, polypropylene and copolymers thereof, the coating is not detrimentally affected by the soil moisture, so the coating will not disintegrate, and remains intact. The pores in the coating allow for a low, substantially constant release rate, and similar to the release exhibited by the coated products described in the '518 patent, and the onset of this release occurs upon application of the product. Commercially available fertilizers which employ the additive approach include NUTRICOTE® fertilizers from Chisso-Asahi Fertilizer Co., Ltd.

U.S. Pat. No. 5,089,041 issued to Thompson et al. Feb. 18, 1992, discloses yet another type of coated fertilizer product which includes a waterborne, polyvinylidene chloride-based latex coating on a water-soluble core. The rate of release is slow and relatively constant, and onset of release begins almost immediately.

Other methods of controlling release employ microcapsules of active ingredients which are soluble in organic solvents. U.S. Pat. No. 4,670,250, issued to Baker Jun. 2, 1987 discloses microcapsules that are prepared from thermoplastic polymers such as polysulfones, polycarbonates and poly(styrene-acrylonitrile)polymers. Again, the active ingredient is delivered at a slow and relatively constant rate.

As illustrated above controlled release products have been developed in several technical fields, especially fertilizers. As also illustrated, the degree of control of release of the fertilizers has mainly been limited to reducing the release rate of active agents, thereby preventing large amounts of fertilizer from being released too early. Such low rates however are also usually continuous for the fertilizer's period of usefulness. In instances where it would be advantageous to increase the rate of fertilizer release after that initial period of slow release, such slower release products do not maximize delivery of fertilizer. In those instances it would be preferable to have a product for which the onset of agent release is delayed for the period of time necessary, but for which at a later, predetermined time substantial release began. Also, a long-term product should be able to provide a period of nearly complete cessation of release during the dormant periods of deep winter and summer.

SUMMARY OF THE INVENTION

It is thus an object of this invention to obtain a product having a higher degree of control of the rate of release of active agents. Such a product comprises (a) a core comprising at least one water soluble agent;

(b) a first coating layer which is intermediate to (a) and layer (c), wherein said layer has the ability to release (a) at a controlled rate; and (c) a second coating layer which encapsulates (a) and (b) wherein said layer (c) has a water vapor transmission rate of 2.5 g/m²/day or less.

Another object of this invention is to provide a product made of an active ingredient and a carrier, so that the active ingredient is releasable to the environment at different rates at different times. Such a product may have one rate of release during one period, and a different rate of release during another period. Thus the product has a variable rate of release over time which may be tailored to the seasonal variations in a plant's nutritional requirements.

Another object of this invention is to provide a fertilizer product which need be applied only once per predetermined term, such as a growing season (nine months to one year) or multiple years.

BRIEF DESCRIPTION OF THE DRAWINGS

FIGS. 1–13 illustrate release profiles for controlled release fertilizers prepared according to the invention.

DETAILED DESCRIPTION OF THE INVENTION

Figure 1:
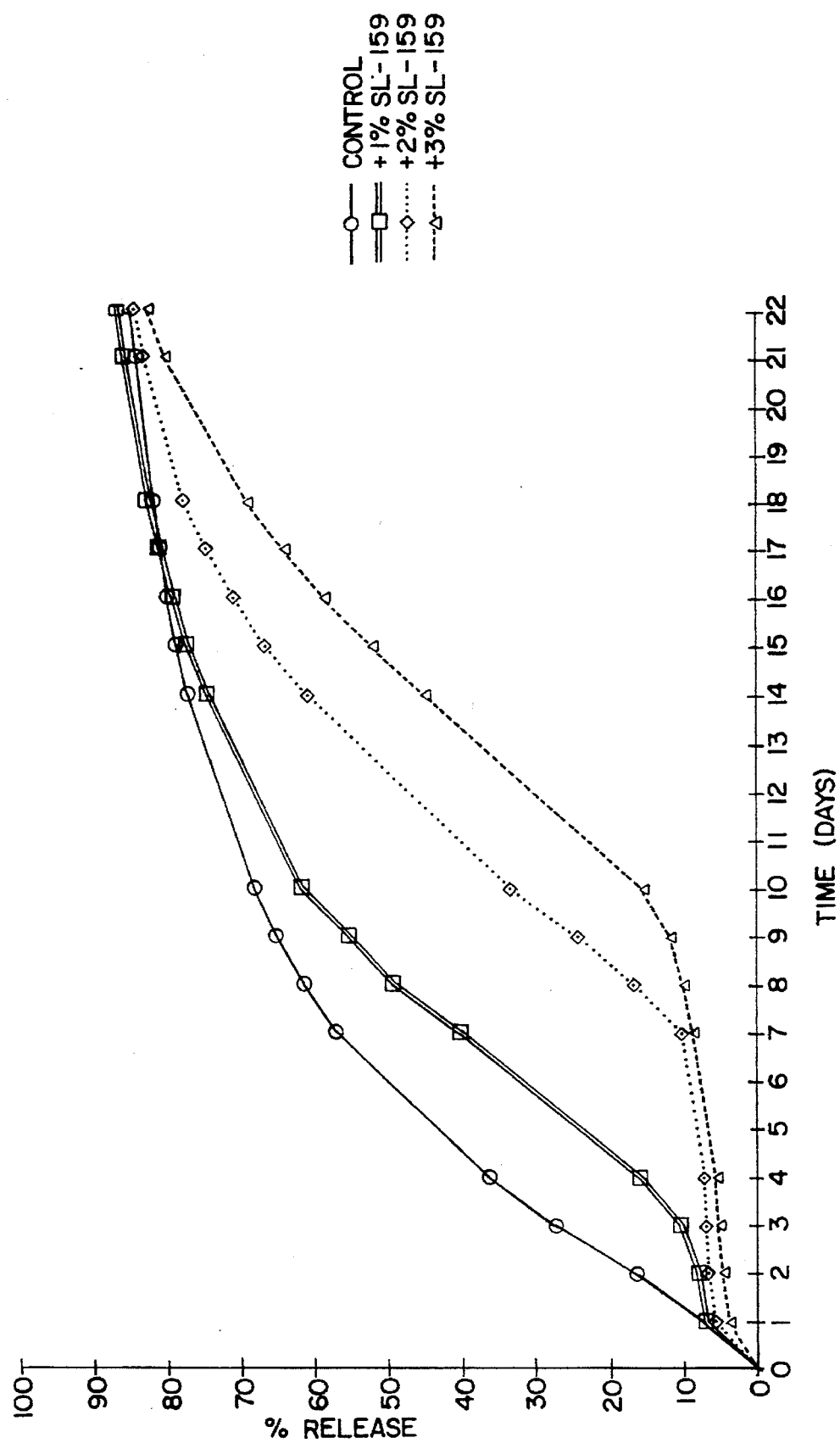

As mentioned above, this invention relates generally to the controlled release of water soluble agents. While the invention is illustrated and described below with reference to an embodiment which employs water soluble fertilizers, the invention can be used for products containing other water soluble agents. Such agents include those that are biologically or horticulturally active agents such as, but not necessarily limited to, pheromones, biofouling inhibitors, insecticides, herbicides and pharmaceuticals. Other agents include pigments, deodorants, fragrances and flavors, corrosion or scale inhibitors, catalysts, chemical additives, etc.

As with many controlled release products the product of this invention comprises a core of water soluble agent. Such cores are obtained in granule or prill form and will likely possess crevices and other surface disfigurations. For this invention, the water soluble agent should have a water solubility equal to or greater than about 1 gram per liter.

When the invention is used for fertilizers, the core will comprise minerals or organic materials which are in a form directly or indirectly assimilable by crops or vegetation. For instance, suitable fertilizer materials contain carbon, nitrogen, oxygen, phosphorus, sulfur, potassium, calcium, magnesium, manganese, zinc, copper, boron, chlorine and other trace elements. See The Yearbook of Agriculture, U.S.D.A. 1957, p. 81. Urea is frequently used. Also available are prefabricated water soluble or soil activated compounds of nitrogen, phosphorus and potassium prepared as granular heterogenous aggregates of various crystalline form which are usually acidic in nature and which have porous, rough and glassy surfaces of irregular configuration are especially preferred. The particular granular aggregates with which this invention is concerned also include such single component fertilizer and explosive ingredients classified as high analysis fertilizers. Such materials contain nitrogen, potassium, and phosphorus-based compounds. Exemplary compounds have well-known designations of 8-24-12, 8-8-6, 5-20-20, 12-12-12, 14-16-0, 4-8-6, 3-9-6, 39-0-0, 9-39-0, in terms of N, $P_2O_5$ and $K_2O$. These materials may also contain supplementary additives such as trace elements, iron salts, insecticides, herbicides, fungicides, growth inhibitors, etc. For instance, one or more suitable herbicides include derivatives of phenoxyacetic acid, phenoxypropionic acid, phenoxybutyric acid, 4-amino-3,5,6-trichloro-picolinic acid, phenoxyethyl sulphuric acid, halogenated benzoic acid, halogenated acetic acid, halogenated propionic acid, phenylurea, or bipyridylium, and certain mineral salts of sodium chlorate, sodium or potassium 2,4-dichlorophenoxyacetate, sodium or potassium 4-chloro-2-methylphenoxyacetate, sodium or potassium 2,4,5-trichlorophenoxyacetate, sodium or potassium 2-(4-chloro-2-methylphenoxy)-propionate, sodium or potassium 2-(2,4-dichlorophenoxy)-propionate, sodium or potassium 4-(2,4-dichlorophenoxy)-butyrate, sodium or potassium 4-(4-chloro-2-methylphenoxy)-butyrate, sodium or potassium 4-(2,4,5-trichlorophenoxy)-butyrate, sodium or potassium 4-amino-3,5,6-trichloropicolinate, sodium 2-(2,4-dichlorophenoxy)-ethylsulfate, 2,3,6-trichlorobenzoic acid, 3,6-dichloro-2-methoxybenzoic acid, sodium chloracetate, trichloracetic acid, sodium 2,2-dichloropropionate, sodium 2,2,3-trichloropropionate, N,N-dimethyl-N'-phenyl urea and its trichloracetic salt, the trichloracetate of N,N-dimethyl-N'-(4-chlorophenyl)urea, copper sulphate, iron sulphate, 1,1'-dimethyl-4,4'-bipyridylium dichloride, 1,1'-bis(3,5-dimethyl-4-morpholinyl)-carbonylmethyl-4,4'-bipyridylium dichloride, 9,10-dihydro-8α,10α-diazaphenanthrene dibromide, 3-amino-1,2,4-triazole, and symmetrical triazines falling under the formula

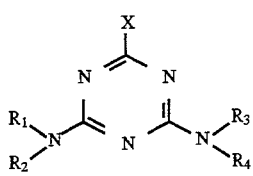

in which X is chlorine, methoxy or methylthio, $R_1$, $R_2$, $R_3$ and $R_4$ are the same or different and are each hydrogen or an alkyl residue containing 1-5 carbon atoms in branched or straight chain and optionally bearing a methoxy group.

The cores can comprise a mixture of two or more of the above elements.

In most cases, the core can also contain certain inert material. These materials include, but are not necessarily limited to, dried clay, calcium carbonate, brick, pumice, pyrophyllite, sulfur, kaolin, dolomite, plaster, wood flour, sugars, sodium chloride or sodium sulfate.

As indicated above, fertilizer cores are available in granule or prill form. For this invention, uncoated fertilizer products in these forms are readily available and are suitable for coating according to this invention.

As mentioned above, there is a first coating layer which encapsulates the core and which is intermediate to the core and the second coating layer described later below. The first layer should be able to release water soluble agent(s) from the core at a controlled rate desired for the particular application contemplated. For instance, if the agent is a fertilizer, the rate at which the agent is released should be such that the vegetation being fertilized is sufficiently nourished. The term "rate of release" of the agent refers to the rate at which the agent is released from the outer surface of the first coating layer. Coatings with such controlled release rates are well known in the art. See U.S. Pat. No. 3,223,518, the contents of which are incorporated by reference. Suitable controlled release rates can be as high as 55% release of the core in 24 hours or as low as 0.05% release of the core in 120 hours. The preferred rate will depend on the application of the fertilizer.

Materials suitable for preparing the first coating layer include organic film forming thermoplastic or thermosetting compounds such as linseed oil; bodied linseed oil; copolymer oils such as dicyclopentadiene copolymer of bodied or unbodied linseed oil; long, medium and short oil alkyds; varnishes; phenol formaldehyde resins; furfuryl alcohol resins; urea formaldehyde resins; butadiene linseed oil copolymers; dicyclopentadiene soybean oil copolymers; dicyclopentadiene soybean oil copolymers wherein the soybean oil has been modified by reaction with maleic anhydride and pentaerythritol; mixtures of dicyclopentadiene linseed oil copolymers and dicyclopentadiene soybean oil copolymers; resin modified alkyds; heat treated or blown oils; alkyds prepared from isophthalic acid materials at various drying oil lengths; silicone alkyds; copolymer alkyds prepared from dicyclopentadiene, styrene, acrylates, and the like; esters of rosin, glycerol, pentaerythritol and other polyols; depolymerized Congo resins and esterification products thereof; phenolic and modified phenolics; modified maleic resins; coumarone-indene resins; terpene resins; petroleum resins, synthetic latices of polymers such as polyvinyl chloride, polyacrylate, polymethacrylate, polyvinyl acetate, copolymers of vinyl acetate and vinyl chloride, butadiene-styrene copolymers, butadiene-acrylonitrile copolymers, vinylidene chloride-vinyl chloride copolymers; melamine formaldehyde; mixed urea-melamine formaldehyde; nitrocellulose; cellulose acetate; ethyl cellulose; condensation products of fatty dimer or trimer acids with diamines; epoxidized materials cured with acids, half esters or anhydrides; condensation products of epichlorohydrin and bisphenol cured with a polyamine; polyesters such as the reaction products of dibasic acids, glycols and styrene; polysiloxane such as the reaction products of silicone chloride with fatty alcohols and other alcohols; petroleum and coal tar pitches and asphalts forming resins when modified with drying and bodied drying oils, or "Epon", etc. Coatings from one or more film forming organic solids melting above 150° F. (65° C.), such as paraffin, natural and synthetic waxes which may be blown or modified, fatty keto esters, dodecyl allophonate, triglycerides of hydroxy stearate of hydrogenated castor oil, polyvinyl stearate, and high melting polyethylenes are also useful. In addition, coatings prepared from molten sulfur are suitable. The first coating layer can be applied by conventional incremental or continuous coating techniques.

The amount (thickness) of first coating layer present will depend on several factors. Because the coating thickness of the first layer will have a significant effect on the release rate, the desired release rate will primarily determine the amount of the first coating. The amount of coating suitable for the desired rate can be obtained through any one of the coating methods described above. Generally, the thicker the coating, the slower the rate. As shown in the Examples which illustrate accelerated testing, the release rate is also influenced by the temperature at which the coated product is used. Generally, the higher the temperature the faster the rate.

The amount of the first coating used will also depend on other factors, including, but not necessarily limited to, the degree of solubility of the water soluble agent to be coated and the surface area of the agent. Amounts of 0.5 to 30%, preferably about 2 to 6%, by weight of the agent are typically suitable for this invention.

The release from such coatings is usually initiated after exposure to moisture which causes the osmotic pressure within the coating to increase to a point where the coating ruptures. The coating is further formulated and designed so that upon rupture, a controlled release of agent occurs. Generally, no more than a week elapses from the time of initial exposure to moisture to the time water soluble agent is released from the first coating.

Precoated prills or granules having a coating layer described above are readily available as Osmocote® fertilizers from Grace-Sierra, Inc. and are particularly suitable for use in this invention.

As indicated earlier, the second coating layer should have a low water vapor transmission rate. This feature is essential for delaying substantial release of the water soluble agent in the product's core. For instance, if the coating had a relatively high water vapor transmission rate, vapor would permeate the product relatively quickly, thereby causing pressure to build up rapidly within the product. At some point the internal osmotic pressure will be high enough to cause the second coating to crack and disintegrate, thus exposing the first layer. Shortly thereafter, and thus shortly after the initial exposure to moisture, the product would begin to release the agent. In effect, a product coated with a high water vapor transmitting material would have a controlled release rate essentially the same as a product coated only with the first layer.

On the other hand, by using a second coating having a relatively low water vapor transmission rate, i.e. equal to or less than 2.5 g/m²/day, as measured by ASTM E96-80, osmotic pressure within the product builds up slowly. It is only after one month or later that the pressure is sufficient to rupture the second coating, thereby creating the onset of release. As indicated earlier, once substantial release is initiated, its rate would parallel with the release rate from the first layer if used alone.

For the most part the vapor transmission rate is affected by the resin used to make the coating and the coating's thickness. For example, a certain thickness of vinylidene chloride copolymers has a lower vapor transmission rate than a polyethylene coating of the same thickness. Even further, thicker coatings provide for lower water vapor transmission rates. Accordingly, the resin selected for the coating and amount (thickness) of coating should be sufficient to provide a water vapor transmission rate equal to or less than 2.5 g/m$^2$/day. An even more preferred rate is 1.0 g/m$^2$/day or less. Amounts of 3% by weight of the water soluble agent are particularly preferable for most resins, but can be lower, e.g. 1% by weight, for others, e.g. poly(vinylidene chloride) copolymers.

Layers having water vapor transmission rates appropriate for the second coating can be prepared from various thermoplastic resins. Such resins include, but are not necessarily limited to, aromatic vinyl compounds such as polystyrene, and copolymers thereof such as poly(styrene-acrylonitriles), acrylonitrile-butadiene-styrene polymers; amides such as acrylamide and methacrylamide; polyamide-imides; polyimides; aliphatic dienes such as polybutadienes; polymers prepared from unsatursuch as (meth)acrylds such as (meth) acrylic acid, crotonic acid, fumaric acid and itaconic acid, salt or esters thereof; polyolefins such as low density polyethylene, medium density polyethylene, high density polyethylene, atactic(amorphous)polypropylene, isotactic (crystalline)polypropylene, ethylene-propylene copolymer, propylene-butylene copolymer; polyvinyls prepared from halogen substituted vinyl compounds such as vinyl chloride, vinylidene chloride, vinyl fluoride, vinylidene fluorides; polyacrylonitriles; polyethylene-terephthalates; polybutylene-terephthlates; polyacetals; cellulose esters; polyurethanes; polyacrylates; vinyl carboxylic esters such as vinyl acetate; and polyaryl ethers.

Vinylidene chloride-based thermoplastics are particularly preferable, especially copolymers with acrylates, methacrylates and acrylonitrile.

The second coating is applied after the first coating layer has been cured and can be applied by conventional coating techniques, such as pan or fluidized bed coating techniques. The second coating can also be the result of one or more applications of the resins described above, as more fully described in U.S. Pat. No. 4,019,890, the text of which is incorporated herein by reference as if set forth in full.

As is apparent from the above, the invention can be prepared by providing a coating (b) onto fertilizer products already provided with a coating (a), e.g. Osmocote® fertilizer available from Grace-Sierra Horticultural Products. By providing coating (b) on such products the onset of release can be delayed well beyond the week delay typically exhibited by those commercial products. Accordingly, this invention allows one to prepare a delayed release product simply by applying the second coating (b) to products having a preexisting coating.

For many fertilizer products, it is preferable that substantial release of fertilizer is delayed until at least a month and sometimes as long as one or two years. For instance, such fertilizers would be beneficial for the seedlings which typically do not require fertilizer during the first year after planting.

For this invention, substantially "delayed" release occurs when no more than about 10% of the fertilizer product is released after a month or more from the time the product is applied. After one month or more, the onset of release occurs, with the release rate of the product being the release rate of the first coating when used alone. In some instances, up to about 10% of the agent is "released" from the product in less than a month because of insufficient initial coatings. Therefore, such release should not be considered as onset of release and would be better considered as "background" release which will usually not affect the target of the product.

In the agricultural industry, delayed, controlled release is particularly advantageous. For many agricultural products, seeds are planted during spring, with fertilizer usually laid down at a later time. If a delayed, controlled release fertilizer product is employed, the fertilizer and seed can be distributed at the same time. Such products would allow the simultaneous application of seed and fertilizer with little harm to the crop in its early stage of development because of the initial delay in release of the fertilizer. However, the release is only delayed as long as the second coating is intact. When that layer disintegrates, onset of substantial release will occur, with the release rate coinciding with the rate of the first coating. Typically, the first coating will deliver fertilizer at the maximally effective rate.

Another aspect of this invention is that a product can be made that provides a moderate initial nutrient release followed by a longer-term, fairly constant nutrient release. The amount of the initial nutrient release varies with the thickness of the inner coating and the temperature at which the second coating is applied. The longevity of the product may be varied by changing the thickness of the outer coating and its water vapor transmission rate.

In this procedure the substrate prills are first coated with prepolymer of dicyclopentadiene and a vegetable oil such as linseed oil or soybean oil until the coating weight is approximately 1–12%, preferably 2–6% of the weight of the prills. The second polymer coating is applied in the range of 0.5–10%, preferably 1–5% by weight of the prills using an aqueous emulsion resin with very low water vapor transmission. The aqueous emulsion could be made of vinylidene chloride/acrylate(methacrylate) type of copolymer. The second coating can be applied from 30°–55° C.; the lower the coating temperature the higher the initial release. During the application of the second coating some of the nutrient are dissolved in the leftover water of the coating particle. The soluble materials thus get embedded into the polymer matrix and therefore act as pore formers in the coating. This means that pore formers can be introduced into the polymer matrix in situ. The initial release can be controlled by controlling the thickness of the inner or outer coatings. The longevity of the product is varied by varying the water vapor transmission and/or the thickness of the outside coating. As a result, variables introduced into a single manufacturing process w(which applies two coatings) can be used to produce a variety of products which meet the specific nutrient requirements of different crops.

If the initial coating is thicker, then the second coating provides a product which releases no nutrient initially and the release of the substrate is delayed. The delayed release products are discussed in patent application U.S. Ser. No. 733,891, filed Jul. 22, 1991 and now abandoned, and incorporated herein as if set forth in full.

In the alternative, a pattern can be established where no nutrients are provided to the plant at a time when the plant is dormant. Blending of delayed release products with conventional controlled release products can provide an "on-off-on" "on-on" and "off-on" products. So, a nine month product can be prepared which release nutrients in the spring and fall, but not in the summer. This is a distinct advantage because the existing controlled release technology is heat sensitive and tends to over-release during the sumer. A 1:1 blend of 3–4 month conventional Osmocote product available from Grace-Sierra and a 6-month delayed release product with a longevity of 3–4 months could be applied in the spring. The nutrient release would occur in spring and fall with very little release during the summer period. During the summer plants are close to dormant and therefore do not take up nutrients to any great degree. At this stage, it is possible to harm the plants by excess release of nutrient salts. Also, the excess can be washed by rain water into rivers and lakes. Naturally, it would also be possible to apply the type of product in the fall, to provide nutrient release in the fall and spring only.

In yet another embodiment of this invention, a fertilizer nutrient system can be provided that is custom tailored to the needs of various crops. By incorporating delayed release products with the existing nutrient feed systems, one can provide specific nutrients to the plants at a definite time. For example, a high dose of potassium can be delivered to plants during the flowering stage.

While the invention is described with preferred embodiments, it is to be understood that variations and modifications may be resorted to as will be apparent to those skilled in the art. Such variations and modifications are to be considered within the purview and the scope of the claims appended hereto.

EXAMPLE 1

Urea prills, 50 g, which had been coated with a linseed oil/dicyclopentadiene copolymer at approximately 11% by weight of the prills were heated to 80°–90° C. in a fluidized bed coater. An aqueous emulsion of DARAN® SL-159 poly(vinylidene-chloride/acrylate) from Organic Chemicals Division of W. R. Grace & Co.-Conn. was added at 1, 2 & 3% based on the prill weight. The coatings contained 10% (based on coating weight) talc to reduce prill agglomeration. The release profile of the dual coated product was then tested alongside the linseed oil/dicylcopentadiene copolymer coated fertilizer described above. To measure the release profile of the coated fertilizers, 3.0 g coated fertilizer is mixed with 500 g of sand and placed in a filter funnel. The mixture is then wetted with 75 ml of deionized water, sealed, and the apparatus is placed in an oven at 50° C. (accelerated test). At 24 hour intervals, the water containing the dissolved urea is filtered off. The sample/sand mixture is rinsed with 50 ml of pure deionized water and the two aliquots are combined. The solution concentration is then measured colorimetrically using the Blood Urea Nitrogen (BUN) assay. By dividing this value by that obtained for the maximum concentration (i.e. 3.0 g urea/125 ml), the percentage release is determined. As illustrated in FIG. 1, the release profiles are significantly altered, thus providing an ability to tailor release to specific applications.

EXAMPLE 2

Figure 2:
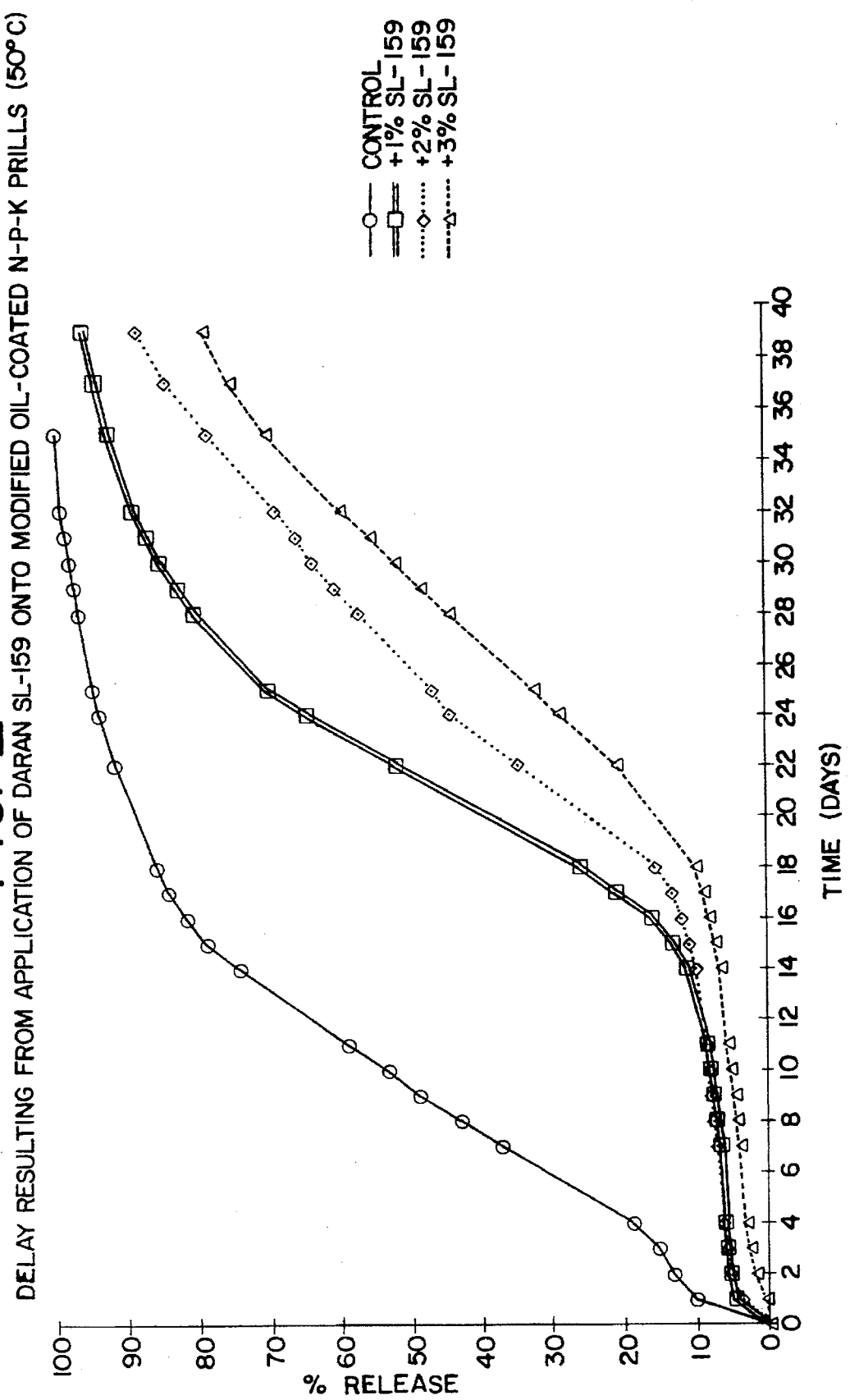
Figure 3:
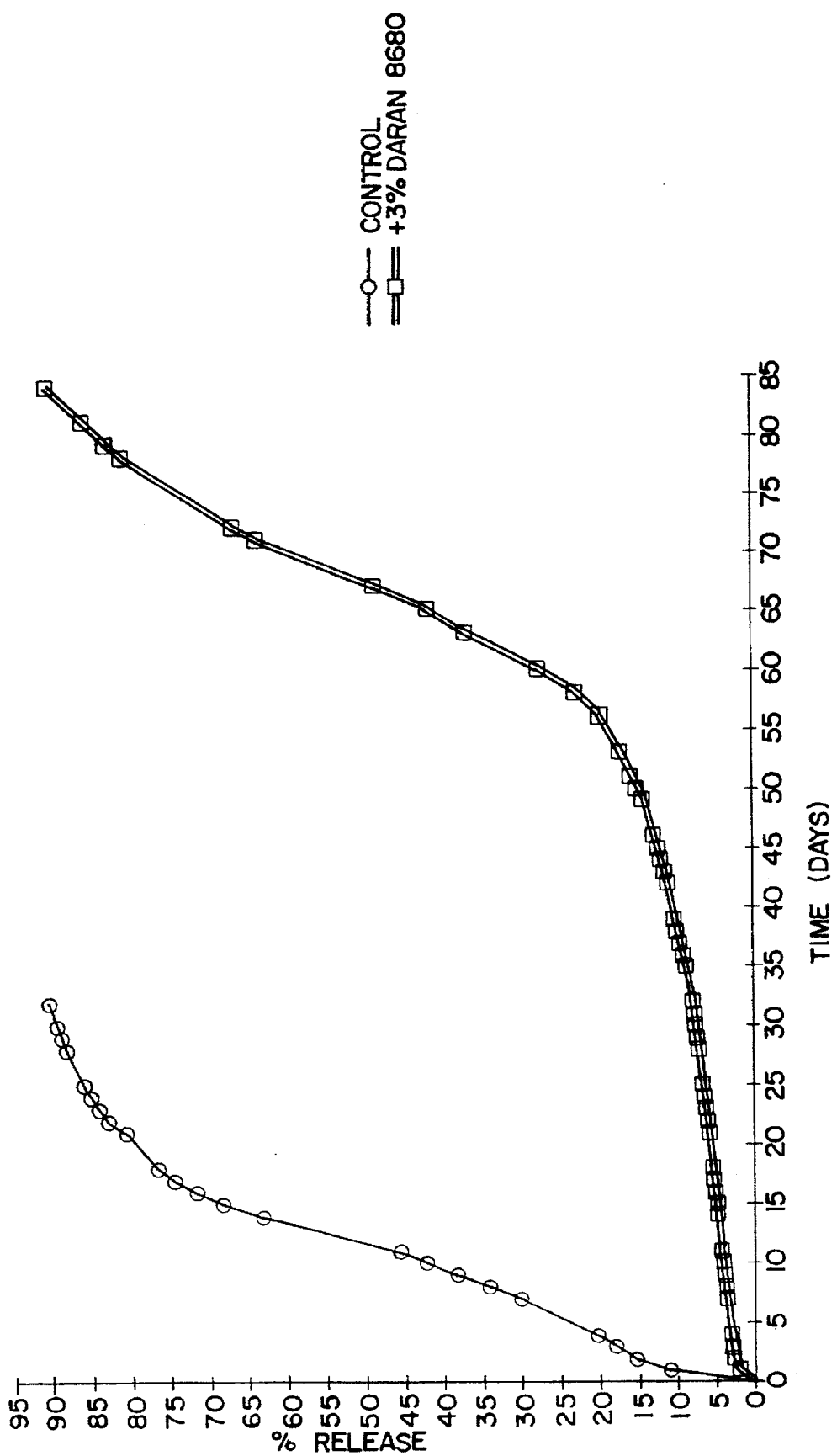
Figure 4:
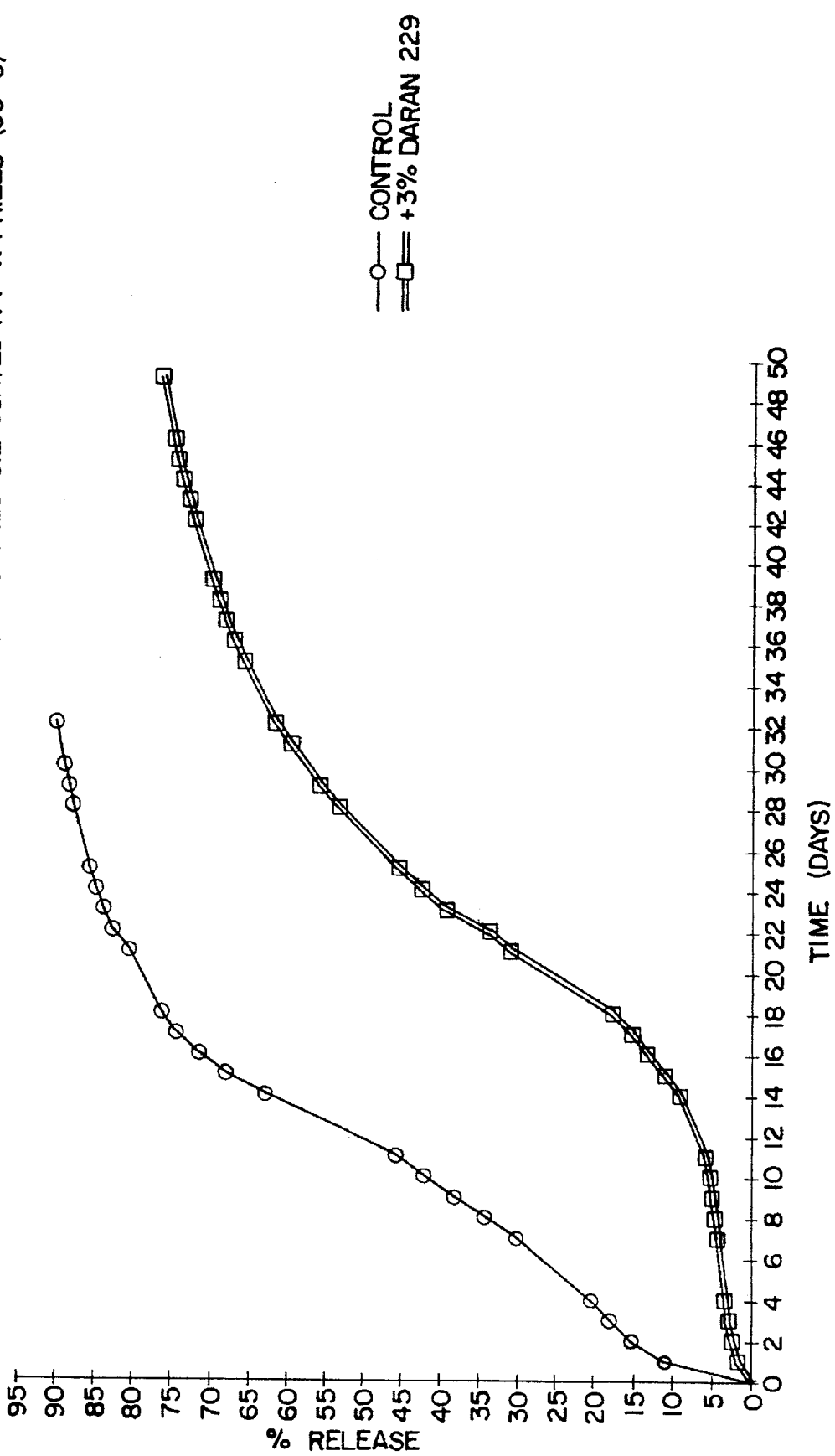
Figure 5:
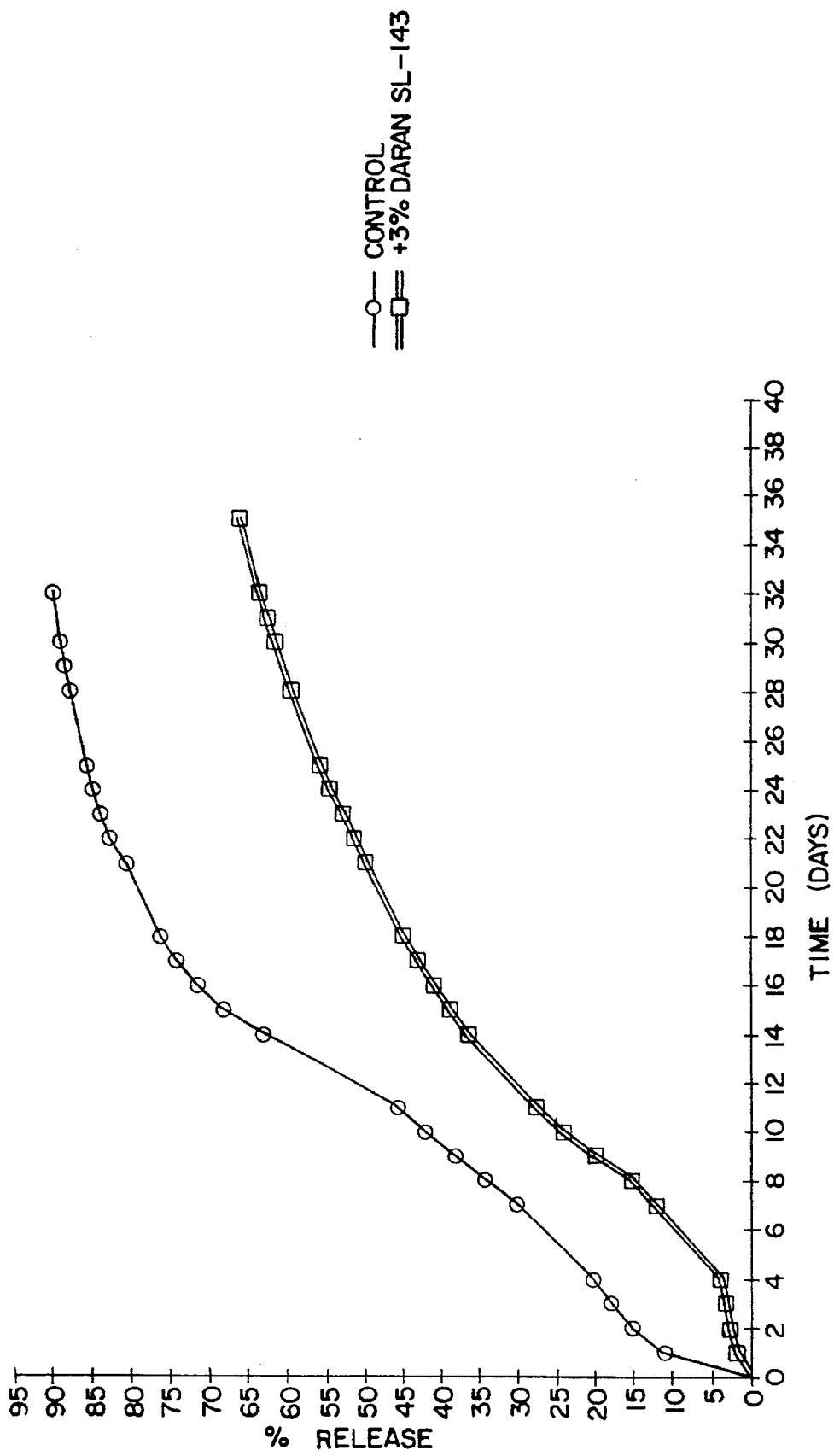

A linseed oil/dicyclopentadiene-coated NPK 17-7-12 fertilizer from Grace-Sierra Horticultural Products Co. was coated in the manner described in Example 1. Based on accelerated testing similar to that described in Example 1, samples without the emulsion coating released 60% of their nutrients in eleven days, where the 1, 2 & 3% emulsion coatings of the invention have released 9, 9 & 6%, respectively. See FIG. 2. The release profile of the NPK product was measured using the same preparation method described above, except that the solution concentrations were determined by conductivity measurement.

EXAMPLES 3–6

Coated NPK 17-7-12 fertilizer samples described in Example 2 were coated in the same manner as that described in Example 2 except the following copolymers were applied in an amount of 3% by weight of the fertilizer product as a substitute for DARAN® SL159 copolymer.

Example 3: DARAN® 8680 poly(vinylidene chloride/methacrylate/methyl methacrylate) from the Organic Chemical Division of W. R. Grace & Co.- Conn.

Example 4: DARAN® 229 poly(vinylidene chloride/methacrylate/methyl methacrylate) from the Organic Chemical Division of W. R. Grace & Co.- Conn.

Example 5: DARAN® SL-143 poly(vinylidene chloride/methacrylate/methyl methacrylate) from the Organic Chemical Division of W. R. Grace & Co.- Conn.

Example 6: DARAN® SL-112 vinylidene chloride/methyl methacrylate/acrylonitrile

The release profiles of the resulting coated fertilizer products were then measured using the techniques described in Example 2 above. These profiles are provided in FIGS. 3–6 for Examples 3–6 respectively.

EXAMPLE 7

Coating of Fertilizers Prills Containing NPK

NPK prills of the composition 15-15-15 (15% N, 15% $P_2O_5$ and 15% $K_2O$) that had been coated with linseed oil/dicyclopentadiene copolymer at approximately 3% by weight of the prills were heated in a fluidized bed at 80°–90° C. An aqueous emulsion of poly(vinylidene-chloride/acrylate) was added at 1, 1.5 and 2% based on the prill weight. The bed temperature dropped down to 50°–55° C. soon after the aqueous emulsion was first applied. The temperature was maintained at approximately 50° C. during the coating which took about 15 minutes. The testing was carried out in an accelerated sand leach test at 50° C. The release of the nutrient was monitored by determining conductivity of the leachate.

The release profiles were significantly altered. This demonstrates the ability to obtain a moderate to high initial release followed by a low, relatively constant release. That is, one can select an initial level of release as well as a period of longevity. FIG. 7 shows a daily release profile, i.e., percentage of the total amount of releasable nutrients contained in each separate sample, for the control ("15-15-15"-3% linseed oil/dicyclopentadiene copolymer coating only) and various levels of the second coating. FIG. 7 shows that the initial release can be reduced from about 54% (control: no second coat) to 17% (2% coating SL159). The lower initial release is coupled with a different long term release. What appear to be slight differences in FIG. 7 with respect to long term release are nonetheless significant to the plants and are better illustrated in FIG. 8.

FIG. 8 shows the same results as cumulative release. For the purposes of this analysis, release is considered to be substantially complete when the cumulative total reaches 80%. Thus, one can see that the control is fully depleted within about three days, while a 1% added coating has only 50% release at three days. The material with the 1% added coating had only reached about 75% release after 14 days. It is clear that after the initial release of high nutrient concentration the release rates slow down and the product with longevity of 3, 6, 9 or 12 months can be prepared.

EXAMPLE 8

The identical conditions were employed to coat urea product having linseed oil/dicyclopentadiene based coating level of 3.4 parts of coating per hundred parts fertilizer by weight ("pph") with aqueous emulsion at the level of 3 and 5% pph. The accelerated release profile is shown in FIG. 9. Again, the release pattern for these products is similar to the one seen for products of Example 7, where initial high release is followed by a slow zero order (linear or constant rate) release for both the products to provide products with extended longevity. The release profile for the two products is almost parallel after the initial release. Thus the amount of initial release can be controlled by changing the thickness of outer layer. Identical conditions were used to coat the urea product with linseed oil/dicyclopentadiene based level coating of 5.5 pph with aqueous emulsion at a level of 3%. The accelerated release profiles of products of 3.5 and 5.5 pph levels of inner coating and a level of 3% outer coating are shown in FIG. 10. Again, the effect of increasing the total coating weight is to suppress the amount of initial release, but in this case as the thickness of the inner coating is varied the slope of the two curves after initial release are also varied. With both products the release profile after initial release is again nearly linear, or of zero order. Thus by controlling the thickness of the outer coating and inner coating, the initial release and the release rates can be varied to prepare products for use in nursery, greenhouse, turf and vegetation grown in various climates. Thus a product can be prepared for use in turf which can be applied in March and will last for the whole season. This product will have initial high release on the order of 360–720 g nitrogen per 1,000 square feet per month for quick greening of the lawn followed by slow release on the order of 100–250 g nitrogen per 1,000 square feet per month for 6–9 months. After the initial period the release rate would be at a low, constant rate so that enough urea is released to keep the grass green but the growth of the grass is relatively slow, and mowing intervals are longer than the practice used presently.

One of ordinary skill in the art will recognize that the rate of release measured in grams of nitrogen is merely a convenient form of measurement used in the industry. In principle, the rate of release can refer to any active ingredient.

EXAMPLE 9

Patterned Release Product: An ideal controlled release product would be the one that responds to the needs of the plant. An ideal product for a grower would be one that responds to the needs of the plant and could be introduced into the soil during the potting of the plants. Some growers pot so many plants that it is labor intensive to top dress, or add fertilizer to the container, after the first potting. Thus for example it may take up to 2 months for three people to top dress in the fall after potting in the spring. Because the cost involved in top dressing in the Fall this method is not followed and a nine-month product to carry over to the fall is employed. Thus an ideal product should respond to plant need and have a longevity of the whole season (or one year). If potting is to be carried out in the spring, an ideal fertilizer should release nutrients during the spring with a low level of release during the summer season and high level of nutrient release again during the fall. The product would need to supply the nutrient requirement of the plant for nine months. Most commercial products release the majority of the nutrients in the early part of its lifetime. If these are to be used during Spring potting, the nutrient release occurs during the Spring and Summer with the residual amount releasing during the Fall. A majority of the nutrients tend to release more heavily during the Summer when the temperatures are high. Actually, many plants require a very small amount of nutrient during the Summer because plants become dormant due to the heat, and, in fact, a large amount of nutrient release could hurt plants. Also, the excess tends to be washed away by rainwater and causes environmental problems. A useful product can be prepared by blending a standard controlled release Osmocote type product available commercially and a delayed release product. Such a product can be prepared by using delayed release products described in Example 2. FIG. 11 shows the weekly release profile at 90° F. (average use temperature in Florida) for such a blend. For example, if the plants were potted in March, the maximum release on the order of 400 to 1,000 g nitrogen per cubic yard would occur in week 5–week 12 (April–May) and by the 16th week (end of June) the release of nutrient would be lowest and will stay that way for 8 weeks (July–August) before it increases to a maximum on the order of 300–700 g nitrogen per cubic yard for another 8 weeks (September–October) and then drops during the next 4–5 weeks (November). Such a product would be highly desirable to the nurserymen and would also be a more environmentally benign product. Blending of delayed release products can be similarly extended to 1½-year or 2-year products. In FIG. 12 is shown the release profile at 50° C. of a blend of two delayed release products and a standard Osmocote product to prepare a two-year product. The delayed release products are used from Example 2 and Example 3.

EXAMPLE 10

Flowering annuals are grown in the greenhouse from seeds or cuttings for three months and are put in baskets before they are sold to the stores. These plants stay in the store for a short period of time while they are sold to the consumer who keeps it for 4–5 months. The nutrient requirements for such a plant are different at different stages of its growth. For example, during the three months in the greenhouse, the plant needs only a third of the nutrients compared to that needed for the next three months when it is with consumer, and the requirements for the month 7 and month 8 are again lower than months 4–6. An ideal product for such a use will be one time added product which is mixed in the soil during the potting. Thus neither the retailer nor the consumer has to worry about adding fertilizer after the plant is bought. A blend of delayed release product similar to one described in Example 2 and a standard Osmocote type product would provide the ideal product to be used in the greenhouse for annuals. This blend will consist of 20% by weight of a 3-month standard Osmocote product and 80% of 4–5 month delayed release product with delay of 3 months. According to FIG. 13, this product when used in March would supply the active ingredient during three distinct periods at rates having ratios of about 1:3:2, i.e., 0.5 g nitrogen/pot/month for first three months, the level of nutrient would be 1.5 g nitrogen/pot/month for the next three months (June–August) and 1.0 g nitrogen/pot/month for September and October. In this case a pot would be something on the order of a 10-inch hanging basket, and nominally has a volume of about 0.34 ft$^3$. This product is somewhat different in requirement than that described in Examples 10 and 11 where the maximum amount of nutrients are needed during the Summer since the plant is at the maximum growth stage in its cycle and the consumer adds water more often than the grower of perennials or ornamentals in a nursery.

What is claimed:

1. A controlled release product having a delayed period of onset comprising:

a particulate water-soluble core material selected from the group consisting of fertilizers, pheromones, biofouling inhibitors, insecticides, herbicides, fungicides, growth inhibitors and mixtures thereof;

a first coating layer selected from the group consisting of organic film forming thermoplastic or thermosetting compositions, sulfur and mixtures thereof applied directly onto the surface of said particulate core material for controlling the rate of release of said core material upon dissolution of said core resulting from exposure of said core to moisture; and a second coating layer consisting essentially of a relatively water impermeable material having a relatively low water vapor transmission rate selected from the group consisting of vinyl compounds and copolymers thereof; amides; polyamide-imides; polyimides; aliphatic dienes, polymers prepared from unsaturated carboxylic acids; salts of polymers prepared from unsaturated carboxylic acids; esters of polymers prepared from unsaturated carboxylic acids; polyolefins; polyvinyls prepared from halogen substituted vinyl compounds; polyethylene-terephthalates; polybutylene-terephthalates; polyacetals; cellulose esters; polyurethanes; polyacrylates; vinyl carboxylic esters, polyaryl ethers and mixture thereof applied over said first coating layer and at a thickness such that said second coating layer causes the release of said core material to be delayed for a substantial period of at least four weeks up to a period of two years from first exposure of said product to moisture;

said second coating layer being formulated to burst upon conclusion of said delay period causing said rate of release of said core material through said first and said second coating layers to abruptly increase to a controlled rate of release corresponding essentially to the rate of release of said first coating layer alone.

2. The product of claim 1, wherein the water-soluble core material is selected from the group consisting of plant nutrients, pesticides and herbicides.

3. The product of claim 1, wherein the water-soluble core material is selected from the group consisting of nitrogen, phosphorus, potassium, urea, and sulfur-coated urea.

4. A product according to claim 1 wherein the first coating layer comprises thermoset resin.

5. A product according to claim 1 wherein the first coating layer comprises alkyd resin.

6. A product according to claim 1 wherein the alkyd is linseed or soybean oil-based.

7. A product according to claim 1 wherein the second coating layer comprises thermoplastic resin.

8. A product according to claim 1 wherein the second coating layer comprises vinylidene chloride-based resin.

9. The product of claim 8, wherein the first layer is a vegetable oil/dicyclopentadiene copolymer; and the second layer is selected from the group consisting of copolymers of vinylidine-chloride and (meth)acrylates or vinylidine-chloride, (meth)acrylates, acrylonitrile, and mixtures thereof.

10. The product of claim 8, wherein the first layer is sulfur; and the second layer is selected from the group consisting of copolymers of vinylidine-chloride and (meth) acrylates or vinylidine-chloride, (meth)acrylates, acrylonitrile, and mixtures thereof.

11. The product of claim 8, wherein the first coating layer comprises up to about 12% by weight of the product; and the second layer comprises up to about 10% by weight of the product.

12. The product of claim 11, wherein the first coating layer comprises about 2–6% by weight of the product; and the second layer comprises about 1–5% by weight of the product.

13. A product according to claim 1 wherein the water vapor transmission rate of the second coating layer is 2.5 $g/m^2/day$ or less.

14. A product according to claim 1 wherein the water vapor transmission rate of the second coating layer is 1 $g/m^2/day$ or less.

15. A product comprising a blend including the product of claim 1, wherein the water-soluble agent is releasable during the first period of about 2 weeks at a rate of 360–720 g $N/1,000\ ft^2/month$; during a period of controlled release of about 8–9 months at a rate of about 100–250 g $N/1,000\ ft^2/month$.

16. A product comprising a blend including the product of claim 1 wherein the water-soluble agent is releasable to the environment during more than one period of controlled release.

17. A product according to claim 16, wherein the water-soluble core material is releasable to the environment during at least three periods of controlled release.

18. A product according to claim 17, wherein the water-soluble core material is releasable to the environment during three periods of controlled release in relative amounts having ratios of 1:3:2.

19. A product according to claim 18, wherein the water-soluble core material is releasable during a first period of about three months at a rate of about 1 to 2 g N/month/cubic foot; during a second period of about three months at a rate of about 4 to 5 g N/month/cubic foot; during a third period of about ½ months at a rate of about 2.5 to 3.5 g N/month/cubic foot.

20. A product according to claim 17, wherein the water-soluble core material is releasable during a first period of about four months at a rate of about 400 to 1,000 g N/cubic yard; during a second period at a substantially reduced rate; and during a third period of about four months at a rate of about 300–700 g N/cubic yard.

21. A product according to claim 1 wherein the initial delay period is at least one year.

22. A method of delaying the controlled release of a water-soluble core material which comprises applying to an agricultural or horticultural substrate, a product comprising a particulate water-soluble core material selected from the group consisting of fertilizers, pheromones, biofouling inhibitors, insecticides, herbicides, fungicides, growth inhibitors and mixtures thereof having a first coating layer selected from the group consisting of organic film forming thermoplastic or thermosetting compositions, sulfur and mixtures thereof applied directly onto the surface of said particulate core material for controlling the rate of release of said core material upon dissolution of said core resulting from exposure of said core to moisture; said product having a second coating layer consisting essentially of a relatively water impermeable material having a relatively low water vapor transmission rate selected from the group consisting of vinyl compounds and copolymers thereof; amides; polyamide-imides; polyimides; aliphatic dienes, polymers prepared from unsaturated carboxylic acids; salts of polymers prepared from unsaturated carboxylic acids; esters of polymers prepared from unsaturated carboxylic acids; polyolefins; polyvinyls prepared from halogen substituted vinyl compounds; polyethylene-terephthalates; polybutylene-terephthalates; polyacetals; cellulose esters; polyurethanes; polyacrylates; vinyl carboxylic esters, polyaryl ethers and mixture thereof applied over said first coating layer at a thickness such that said second coating layer causes the release of said core material to be delayed for a substantial period of at least four weeks up to a period of two years from first exposure of said product to moisture and said second coating layer being formulated to burst, upon conclusion of said delay period, causing said rate of release of said core material through said first and said second coating layers to abruptly increase to a controlled rate of release corresponding essentially to the rate of release of said first coating layer alone.

23. The method of claim 22 wherein the product comprises the product of any one of claims 24–43 and 46.

24. A controlled release product having a delayed period of onset comprising:

a particulate water-soluble core material selected from the group consisting of fertilizers, pheromones, biofouling inhibitors, insecticides, herbicides, fungicides, growth inhibitors and mixtures thereof;

a first coating layer selected from the group consisting of organic film forming thermoplastic or thermosetting compositions, sulfur and mixtures thereof applied directly onto the surface of said particulate core material for controlling the rate of release of said core material upon dissolution of said core resulting from exposure of said core to moisture; and a second coating layer consisting essentially of a relatively water impermeable material having a water vapor transmission rate equal to or less than 2.5 $g/m^2/$day applied over said first coating layer and at a thickness such that said second coating layer causes the release of said core material to be delayed for a substantial period of at least four weeks up to a period of two years from first exposure of said product to moisture;

said second coating layer being formulated to burst upon conclusion of said delay period causing said rate of release of said core material through said first and said second coating layers to abruptly increase to a controlled rate of release corresponding essentially to the rate of release of said first coating layer alone.

* * * * *